United States Patent [19]
De Ruijter et al.

[11] Patent Number: 6,062,945
[45] Date of Patent: May 16, 2000

[54] PROCESS FOR REARING BUMBLEBEE QUEENS AND PROCESS FOR REARING BUMBLEBEES

[75] Inventors: Arie De Ruijter, Tilburg; Johannes H. P. Van Den Eijnde, Oisterwijk, both of Netherlands

[73] Assignee: Stichting Landelijk Proefbedrijf Insektenbestuiving & Bijenhouderij Ambrosiushoeve, Hilvarenbeek, Netherlands

[21] Appl. No.: 08/983,087

[22] PCT Filed: Jul. 4, 1996

[86] PCT No.: PCT/NL96/00274

§ 371 Date: Mar. 26, 1998

§ 102(e) Date: Mar. 26, 1998

[87] PCT Pub. No.: WO97/03556

PCT Pub. Date: Feb. 6, 1997

[30] Foreign Application Priority Data

Jul. 14, 1995 [NL] Netherlands .............................. 100803

[51] Int. Cl.$^7$ ............................ A01K 47/00; A01K 49/00
[52] U.S. Cl. ......................................... 449/1; 449/2; 449/8
[58] Field of Search ..................................... 449/1, 2, 7, 8

[56] References Cited

U.S. PATENT DOCUMENTS

| | | |
|---|---|---|
| 314,973 | 3/1885 | Mitchell ...................................... 449/2 |
| 4,651,372 | 3/1987 | Schmidt ...................................... 449/2 |
| 5,695,383 | 12/1997 | Le Conte et al. .......................... 449/2 |

*Primary Examiner*—Michael J. Carone
*Assistant Examiner*—Son T. Nguyen
*Attorney, Agent, or Firm*—McCutchen, Doyle, Brown & Enersen, LLP; Emily M. Haliday

[57] ABSTRACT

The invention relates to a process for rearing bumblebee queens (genus Bombus) by generating a colony with workers in the presence of fertilized eggs and/or larvae, in a room with a controlled climate provided with food, and allowing the colony to grow until bumblebee queens are produced. The process constitutes a significant improvement in the rearing of bumblebee queens. The invention also relates to a process for rearing bumblebees (genus Bombus).

7 Claims, No Drawings

PROCESS FOR REARING BUMBLEBEE QUEENS AND PROCESS FOR REARING BUMBLEBEES

DESCRIPTION

The present invention relates to a process for rearing bumblebee queens (genus Bombus) by generating a colony with workers in the presence of fertilized eggs and/or larvae in a room with a controlled climate provided with food and allowing the colony to grow until bumblebee queens are produced.

This process is known from van Heemert, C. et al., Bee World, 71, 54–56 (1990). According to the known process, unfertilized bumblebee queens are first mated with males in special cages, exposed to $CO_2$ in order to interrupt the diapause, and induced to brood. During brooding, workers are produced first; queens are not produced until after some time a sufficiently large number of workers has been produced to take care of the larvae. Furthermore, the number of queens that are eventually produced is very variable.

The object of the present invention is to provide a process for rearing bumblebees, wherein the queens are produced first, and wherein the average number of queens per colony is higher than occurs in nature or than is obtained by using the known process. These advantages are achieved by the process according to the invention, which is characterized in that subadult and/or adult workers which themselves originate from at least one different colony are brought together. This process has never been used before, probably for fear of agressive behaviour among workers of different origin.

Since according to the invention the colonies are formed in an articial manner, the production of queens is started at an earlier stage. Moreover, the number of queens per colony increases. Another advantage of the process according to the invention is that the colonies are younger and less contaminated at the time of starting the production of queens, thus reducing the chance that the newly produced queens are infected microbially or take in contaminated matter. Consequently, the young queens are of a higher quality. Another advantage of the process according to the invention is that finding and catching the young queens is easier, since there is little brood at the time that the young queens appear, and only few males have been produced at that stage. A significant advantage of the process according to the invention is the fact that it has now become possible in the production of bumblebee queens to select for quality, since the colonies from which the queens are reared can be selected on the basis of their favourable properties. Finally, a considerable economy of labour is achieved by using the process according to the invention, since the time required for tending to and checking the colonies is reduced. Furthermore, the process is more efficient than the prior art process, not only because more bumblebee queens per colony are produced, but also because, as a result of the enhanced quality of the colonies, the mating result of the young queens is improved and fewer queens are lost.

The process constitutes a significant improvement for the rearing of bumblebees. Bumblebees can be used for pollination purposes in agriculture and horticulture. This is important in those cases where said pollination must be carried out by hand, for example in the case of tomatoes. It is known (van Heemert, C. et al., Bee World, 71, 54–56 (1990); van den Eijnde, J., Aligemeine Deutsche Imkerzeitung, 6, 12–14 (1990)) that bumblebees have significant advantages in comparison with the honeybees that are also used for these purposes: bumblebees are larger and stronger and their tongues are longer, which makes them also useful for plants which have flowers whose nectar is difficult to reach; moreover, bumblebees are also active at lower outside temperatures and lower light intensities; finally, unlike honeybees, bumblebees do not have a mutual communication system with regard to alternative forage, so that bumblebees will remain inside a greenhouse with for example tomato plants during the summer months as well, whereas under the same circumstances, honeybees would gather food outside the greenhouse.

With the process according to the present invention, the presence of a fertilized, egg-laying queen is in principle not necessary when bumblebee workers and fertilized eggs and/or larvae from one or more colonies are present. However, according to one application of the invention it is preferable to bring together workers from at least one different colony with a young colony in the eusocial phase, consisting of a fertilized queen, brood and the first born workers.

It has been shown experimentally that a sufficiently large number of bumblebee workers should have been produced or brought together in order to produce a queen, whereby it is preferable to bring together more than 100 workers. Moreover, it is preferred to carry out the rearing process with a worker: fertilized eggs and/or larvae ratio of 0.5÷4.

Furthermore, tests have shown that the best results are achieved when the workers originating from a different colony are first kept in a room without any queen and without brood for one day.

According to one preferred application of the process, brood and workers of different species of bumblebees are brought together. Consequently, the process can also be used to improve the production of queens and the rearing of bumblebees of species which are difficult to rear. To that end, brood of a species which is difficult to rear is brought together with workers from a species which is easier to rear.

The known process is already being used for the year-round rearing of bumblebees. As explained above, the process constitutes a significant improvement in bumblebee rearing. The present invention makes it possible to substantially increase the production of bumblebees, since more bumblebee queens are produced within a shorter period of time. The queens produced according to the invention can be used for rearing more bumblebees. Accordingly, the present invention relates to a process for rearing bumblebees, wherein bumblebee queens are reared by using the process according to the invention.

The invention will now be explained in more detail, by means of the following examples.

EXAMPLE 1

On Mar. 2, 1995, a total of 60 workers from different colonies were collected, brought together and kept in a Liebefelder box without any queen for one day. On Mar. 3, 1995, the workers were placed in a bumblebee box in a room with a controlled climate (under known conditions), and brood in different stages of development from different colonies (1573 and 1575, among others) was added. On Mar. 30, 1995, 15 workers from colony 1583 were added. During the period from April 4 to May 2, 1995, the thus formed colony produced 54 queens. On May 2, 1995, the colony comprised 115 workers, 75 of which had been added and 40 of which had been reared from the added brood.

EXAMPLE 2

A queen (*B. terrestris*) from colony 2008 was induced to brood in a manner known per se. On Jan. 17, 1995, the first workers were born, and the eusocial phase started. On Feb. 14, 1995, colony 2008 comprised 35 workers. On that date, 60 workers from colony 1969 were added, which workers had first been kept without any queen for 24 hours. During the period until Mar. 31, 1995 the thus formed colony produced 154 queens.

EXAMPLE 3

The queen (*B. terrestris*) from colony 2027 was induced to brood in a manner known per se. On Jan. 27, 1995, the first workers were born, and the eusocial phase began. On Feb. 21, 1995, colony 2027 comprised 40 workers. On that date, 60 workers were added, more specifically 39 workers from colony 1968 and 21 workers from colony 1977, which workers had first been kept without any queen for 24 hours. During the period until May 1, 1995, the thus formed colony produced 145 queens.

EXAMPLE 4

A queen of the *Bombus cryptarum* (Fabricius) species was induced in the conventional manner to brood in week No. 15 of the year 1996. On May 17, the first offspring was born and the colony was transferred to a box (2805). On May 22 60, *B. cryptarum* workers from colony 2740 were placed in a Liebefelder box without any queen. On May 23 the queen was removed from colony 2805, and the brood from the Liebefelder box, in which the first 4 *B. cryptarum* workers had just been born, was added thereto, including the 4 workers that had just emerged. The 60 workers from colony 2805 were also added. On May 29 the brood from 2 other Liebefelder boxes, which respectively contained 8 and 5 workers that had just hatched, was added. On June 4, 6 and 13, *B. cryptarum* brood in each case from 2 Liebefelder boxes, was added.

Starting 3 weeks after the addition of workers and brood, the production of queens was started. Between June 13 and 19, 27 queens had already been born.

EXAMPLE 5

On Mar. 11, 1996, 60 workers of the *Bombus terrestris* species were placed in a Liebefelder box. On March 12 the brood from 2 Liebefelder boxes was placed in a rearing box (2700), and the 60 *B. terrestris* workers were added thereto. On March 15, the brood of a brooding *Bombus canariensis* Pérez (1895) queen was added. On March 19, the brood of 2 *B. canariensis* queens was added. On March 22, the brood of a *B. terrestris* queen was added, and on April 2 the brood of 2 *B. canariensis* queens was once more added.

On April 5, the first queens were born. This colony produced a total of 66 *B. canariensis* queens and 35 *B. terrestris* queens.

Comparison of the process according to the invention with the known process

The following results were obtained with colonies which were formed at random, that is, without first selecting colonies having specific desired qualities.

The control group treated according to the known process (that is, without adding workers from a different colony) consisted of 607 colonies (group A). The experimental group (group B) consisted of 73 colonies, using the process according to the invention from the eusocial phase on (analogous to Examples 2 and 3).

Group A produced a total of 13,666 queens, with an average of 22.5 per colony. Group B produced a total of 6133 queens, with an average of 84.0 per colony. Consequently, nearly four times as many queens were produced by using the process according to the invention.

With group B the production of queens started on average 49 days after the start of the eusocial phase, that is, on average 20 days sooner than with control group A (69 days).

The total duration of life of the colonies, measured from the start of the eusocial phase until the end of the production of queens, amounted to 92 days with group A and only 78 days with group B. Thus, the increased production of queens took place within a period of time that was 14 days shorter.

We claim:

1. A process for rearing bumblebee queens (genus Bombus) comprising generating a colony with workers in the presence of fertilized eggs and/or larvae from at least one colony, in a room with a controlled climate provided with food, and allowing the colony to grow until bumblebee queens are produced, wherein subadult and/or adult workers that originate from at least one different colony are brought together with said fertilized eggs and/or larvae.

2. The process according to claim 1, wherein the workers that originate from said at least one different colony are brought together with a young colony in the eusocial phase, consisting of a fertilized queen, brood and the first born workers.

3. The process according to claim 1, wherein more than 100 workers are brought together.

4. The process according to claim 1, wherein rearing is carried out using a workers: fertilized eggs ratio of 0.5–4.

5. The process according to claim 1, wherein the workers originating from said at least one different colony are first kept in a room without any queen and without brood for one day.

6. The process according to claim 1, wherein brood and workers from different bumblebee species are brought together.

7. A process for rearing bumblebees (genus Bombus), comprising rearing bumblebee queens by generating a colony with workers in the presence of fertilized eggs and/or larvae from at least one colony, in a room with a controlled climate provided with food, and allowing the colony to grow, wherein subadult and/or adult workers that originate from at least one different colony are brought together with said fertilized eggs and/or larvae, and using said bumblebee queens for rearing bumblebees.

* * * * *